(12) United States Patent
Ettare et al.

(10) Patent No.: US 7,809,435 B1
(45) Date of Patent: Oct. 5, 2010

(54) ADJUSTABLE WIRELESS ELECTROMYOGRAPHY SENSOR AND SYSTEM

(75) Inventors: Ryan D. Ettare, Morgan Hill, CA (US); Willie O. Wasson, Livermore, CA (US)

(73) Assignee: IQ Biolabs, Inc., San Diego, CA (US)

( * ) Notice: Subject to any disclaimer, the term of this patent is extended or adjusted under 35 U.S.C. 154(b) by 968 days.

(21) Appl. No.: 11/329,778

(22) Filed: Jan. 11, 2006

(51) Int. Cl.
*A61B 5/04* (2006.01)

(52) U.S. Cl. .................................................. 600/546

(58) Field of Classification Search ............... 600/546, 600/300, 509, 508, 372–373, 393–396, 545, 600/382–384; 607/41, 60; 455/426.1, 462, 455/507; 235/462.44; 128/903; 708/841; 324/103 P; 327/50, 58; 360/40, 46, 51, 53, 360/65, 67, 77.08; 375/317
See application file for complete search history.

(56) References Cited

U.S. PATENT DOCUMENTS

| | | | | |
|---|---|---|---|---|
| 5,610,387 | A * | 3/1997 | Bard et al. | 235/462.44 |
| 5,706,222 | A * | 1/1998 | Bonaccio et al. | 708/841 |
| 6,289,245 | B1 * | 9/2001 | Mo et al. | 607/41 |
| 7,187,924 | B2 * | 3/2007 | Ohlenbusch et al. | 455/426.1 |
| 7,206,630 | B1 * | 4/2007 | Tarler | 600/509 |
| 2003/0109905 | A1 * | 6/2003 | Mok et al. | 607/60 |

OTHER PUBLICATIONS

Product Specification, Nordic Semiconductor, entitled "Single Chip 433/868/915 MHz Transceiver nRF905," Jan. 2005.
Summary Document, ATMEL, entitled "8-bit AVR(R) Microcontroller with 8K Bytes In-System Programmable Flash," Jun. 2005.
Website: http://web.ensc.sfu.ca/undergraduate_program, 2004.
Document: KineMyo, with product specification, Aug. 2002.
Document: KinePro, with product information. Mar. 2004.
Document: KineView, with product information. Sep. 2004.
Wireless EMG—KineMyo, Jan. 2002.

* cited by examiner

*Primary Examiner*—Max Hindenburg
*Assistant Examiner*—Brian Szmal
(74) *Attorney, Agent, or Firm*—Workman Nydegger

(57) ABSTRACT

An adjustable, wireless electromyography (EMG) sensor includes a first sensor portion and a second sensor portion. The first sensor portion includes a first measurement attachment point, a wireless transmitter, and a control circuit. The control circuit controls the wireless EMG sensor. The second sensor portion includes a second measurement attachment point. The wireless EMG sensor may also include an adjustable connector that connects the first sensor portion and the second sensor portion. The control circuit controls collection of EMG measurements between the first measurement attachment point and the second measurement attachment point, and controls the wireless transmitter to transmit the EMG measurements having been collected. The control circuit may also control power saving by the wireless EMG sensor.

28 Claims, 8 Drawing Sheets

ADJUSTABLE WIRELESS ELECTROMYOGRAPHY SENSOR AND SYSTEM

BACKGROUND

The present invention relates to electromyography sensors, and in particular, to wireless electromyography sensors.

Electromyography (EMG) is the measurement of bioelectrical signals resulting from muscle activity. EMG may also be referred to as myography. EMG may be performed for the purpose of identifying or treating medical conditions related to the muscles. Such conditions include Parkinson's disease, amyotrophic lateral sclerosis (ALS), and other conditions. EMG may also be performed for therapeutic purposes. Such purposes include the detection or prevention of repetitive stress injury (RSI), the detection or prevention of carpal tunnel syndrome (CTS), and other purposes.

EMG measurements may be collected by the placement of one or more electrodes on a person. The electrodes may be inserted under the skin for closer proximity to muscles (referred to as injection EMG) or may be placed on the surface of the skin (referred to as surface EMG). The electrodes transmit the measurements to an analysis unit through a wired connection or wirelessly. With more than one electrode, the bioelectrical difference between the electrodes may be measured as indicative of the activity of the muscular tissue between the electrodes.

Many types of wireless EMG sensors currently exist. However, such existing devices have numerous limitations that make them undesirable for many purposes for which EMG is desired.

One such limitation of many existing wireless EMG sensors is that the sensors have a fixed distance between two electrodes. Thus, the size of the sensor determines the nature of measurements that can be made. For example, if the sensor is small and the muscle to be measured is large, the electrodes can measure only a portion of the muscle activity. Conversely, if the sensor is large and the muscle to be measured is small, the electrodes will detect muscle activity beyond the muscle activity of the muscle to be measured.

Another limitation of many existing wireless EMG sensors, similar to the above limitation, is that the sensor is relatively small compared to some muscles for which measurement is desired. The sensor is able to make only small-scale measurements that may not be indicative of the total muscle movement. Small-scale voltage difference readings are prone to interference from other local muscle fiber firing. Whether at a resting state or engaged in activity, muscle motor units are always firing to some extent. This occurs in a disorganized fashion. Therefore, a voltage difference that measures a small distance is not useful, since interference from local disorganized firing occurs. Additionally, those prone to neurological degenerative diseases, such as multiple sclerosis, will not yield significant data, as this local disorganized firing is increased to an exaggerated degree. The signal spikes uncontrollably, and the resulting data graph is useless.

One possible solution would be to have a variety of different sizes of EMG sensors. The most appropriately-sized sensor would then be used according to the size of the muscle to be measured. However, such a solution is impractical. First, it would require a large variety of sizes of EMG sensors corresponding to the wide variety of muscle sizes. One size of EMG sensors would be required for the wrist; another size for the thigh; and so on. Second, it would require a large variety of sizes of EMG sensors corresponding to the wide variety of body types. The thigh EMG sensor for a child would differ from that for a professional basketball player.

A further limitation of many existing wireless EMG sensors is a battery life that is shorter than desirable. Such short battery life leads to the need to replace batteries more often than desired, as well as the recognition that a short battery life results from a device that is wasteful of power.

Thus, there is a need for an improved wireless EMG sensor. There is a need for a wireless EMG sensor that is adaptable to a wide variety of muscle configurations and a wide variety of body types. There is also a need for a wireless EMG sensor that is reusable. Further, there is a need for a wireless EMG sensor that conserves battery power.

The present invention solves these and other problems by providing an adjustable, wireless EMG sensor.

SUMMARY

Embodiments of the present invention improve a physician's ability to collect EMG data by providing an adjustable EMG sensor. According to one embodiment of the present invention, a wireless EMG sensor includes a first sensor portion and a second sensor portion. The first sensor portion includes a first measurement attachment point, a wireless transmitter, and a control circuit. The control circuit controls the wireless EMG sensor. The second sensor portion includes a second measurement attachment point. The control circuit controls collection of EMG measurements between the first measurement attachment point and the second measurement attachment point, and controls the wireless transmitter to transmit the EMG measurements having been collected.

According to another embodiment of the present invention, the wireless EMG sensor includes an adjustable connector that connects the first sensor portion and the second sensor portion. The adjustable connector adjusts for a variety of measurement distances between the first measurement attachment point and the second measurement attachment point, where the variety of measurement distances correspond to a variety of muscles to be measured on a variety of measurement subjects.

According to another embodiment of the present invention, the control circuit controls power saving by the wireless EMG sensor by powering down selected components of the first sensor portion.

In accordance with the above features, the adjustable EMG sensor is adaptable to a wide variety of muscle configurations and a wide variety of body types, is reusable, and conserves battery power.

The following detailed description and accompanying drawings provide a better understanding of the nature and advantages of the present invention.

DETAILED DESCRIPTION

Described herein are wireless EMG sensors and related systems. In the following description, for purposes of explanation, numerous examples and specific details are set forth in order to provide a thorough understanding of the present invention. It will be evident, however, to one skilled in the art that the present invention as defined by the claims may include some or all of the features in these examples alone or in combination with other features described below, and may further include obvious modifications and equivalents of the features and concepts described herein.

In the following description, the terms "information", "data" and "signal" are used. These and similar terms are considered to be broadly interchangeable. The term "signal" may be used to refer to analog information, but this usage is not to be considered to exclude digital information. The term "data" may be used to refer to digital information, but this usage is not to be considered to exclude analog information. The term "information" may be used to refer to all of analog information, digital information, and mixed analog/digital information.

In the following description, the terms "block", "circuit", "element", "controller" and "processor" are used. These and similar terms are considered to be broadly interchangeable. A particular function may be implemented with circuits, devices, elements, processors, programmable logic devices, programmable logic arrays, integrated circuits, etc. according to design choice, and are not considered to be limitations of the invention.

In the following description, various methods, steps and procedures are described. The order in which these steps are performed is not fixed, except where a later-numbered step absolutely requires than an earlier-numbered step be completed beforehand. Such completion requirements may depend upon the specific features of the devices implementing the invention. Thus, these steps may be performed in a different order, or in parallel, according to the specific implementation. That the steps are described below in a specific order is done mainly for ease of understanding.

Figure 1:
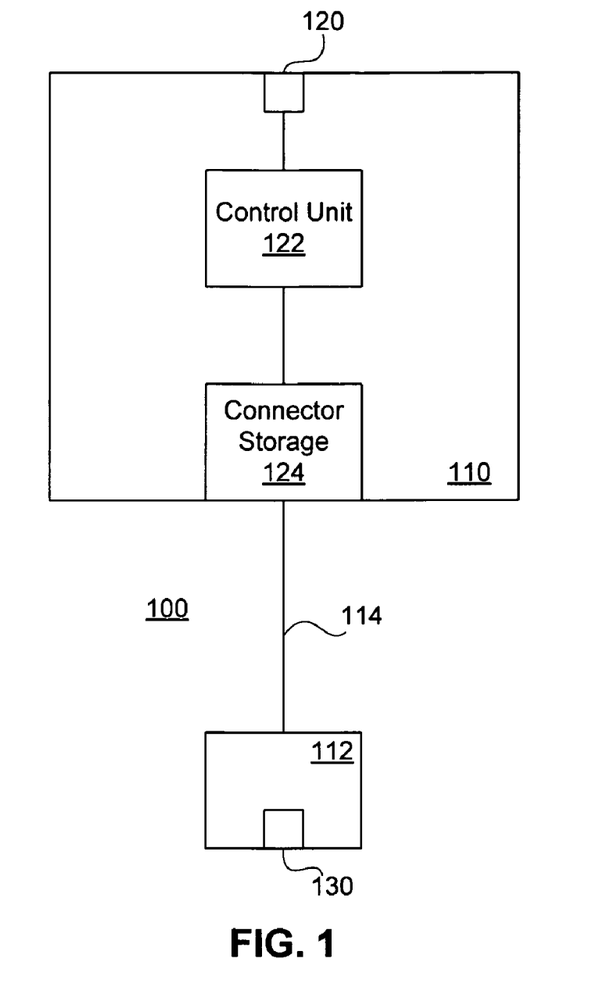
FIG. 1 is a block diagram of an EMG sensor according to an embodiment of the present invention.
Figure 2:
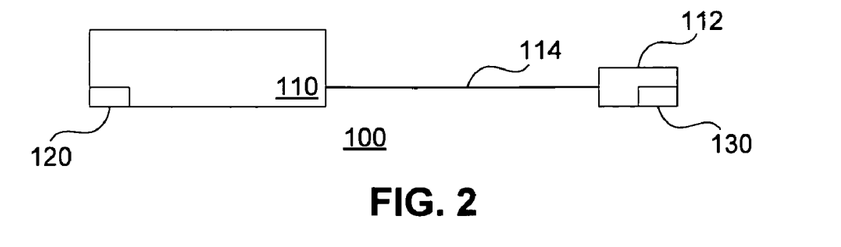
FIG. 2 is a side view of the embodiment shown in FIG. 1.

FIG. 1 is a block diagram of a wireless EMG sensor 100 according to an embodiment of the present invention. The wireless EMG sensor 100 includes a primary sensor unit 110, a secondary sensor unit 112, and a flexible connector 114. FIG. 2 is a partial side view of the wireless EMG sensor 100 shown in FIG. 1. The following description covers the elements necessary for a high-level understanding of the present invention. Lower-level details are described later with reference to additional figures.

The primary sensor unit 110 includes an electrode attachment point 120, a control unit 122, and a connector storage unit 124. The secondary sensor unit 112 includes an electrode attachment point 130. The flexible connector 114 flexibly connects the primary sensor unit 110 and the secondary sensor unit 112 and provides an electrical connection between the electrode attachment point 130 and the control unit 122. The flexible connector 114 is preferably insulated so that the EMG signals are detected via the electrode attachment points 120 and 130, and not through contact by the flexible connector 114 itself.

According to one embodiment, when the EMG sensor 100 is not in use, the connector storage unit 124 winds the flexible connector 114 within under a low tension pull. When the EMG sensor 100 is in use, the primary sensor unit 110 is placed at one location; the secondary sensor unit 112 is pulled forth and placed at a second location; and the connector storage unit 124 maintains a low tension pull on the flexible connector 114. In such an embodiment, the connector storage unit 124 includes a spool around which the flexible connector 114 becomes wound. According to another embodiment, the connector storage unit 124 includes a spindle that may be turned by hand to wind the flexible connector 114. According to yet another embodiment, the connector storage unit 124 and the secondary sensor unit each include a connector attachment point; the flexible connector 114 is selected from one of a number of lengths of flexible connectors according to the desired distance between the primary sensor unit 110 and the secondary sensor unit 112; and the selected flexible connector 114 may be attached at each end to the connector attachment points.

According to a preferred method of use, a first adhesive electrode is attached to the electrode attachment point 120 and to a first point on a person's body, and a second adhesive electrode is attached to the electrode attachment point 130 and to a second point on the person's body. A first set of EMG measurements is then made on the muscle between the first and second points. At a later time, the EMG sensor 100 is moved, and a second set of EMG measurements is made on another muscle. If other muscle is a different size (or is on a differently-sized person) than the first muscle, the flexible connector 114 adjusts as necessary. Additional measurements may then be made using the same EMG sensor 100, with accurate results regardless of the size of the muscle to be measured or the body type of the subject. The EMG sensor 100 is thus reusable, with only the adhesive electrodes involving replacement.

Figure 3:
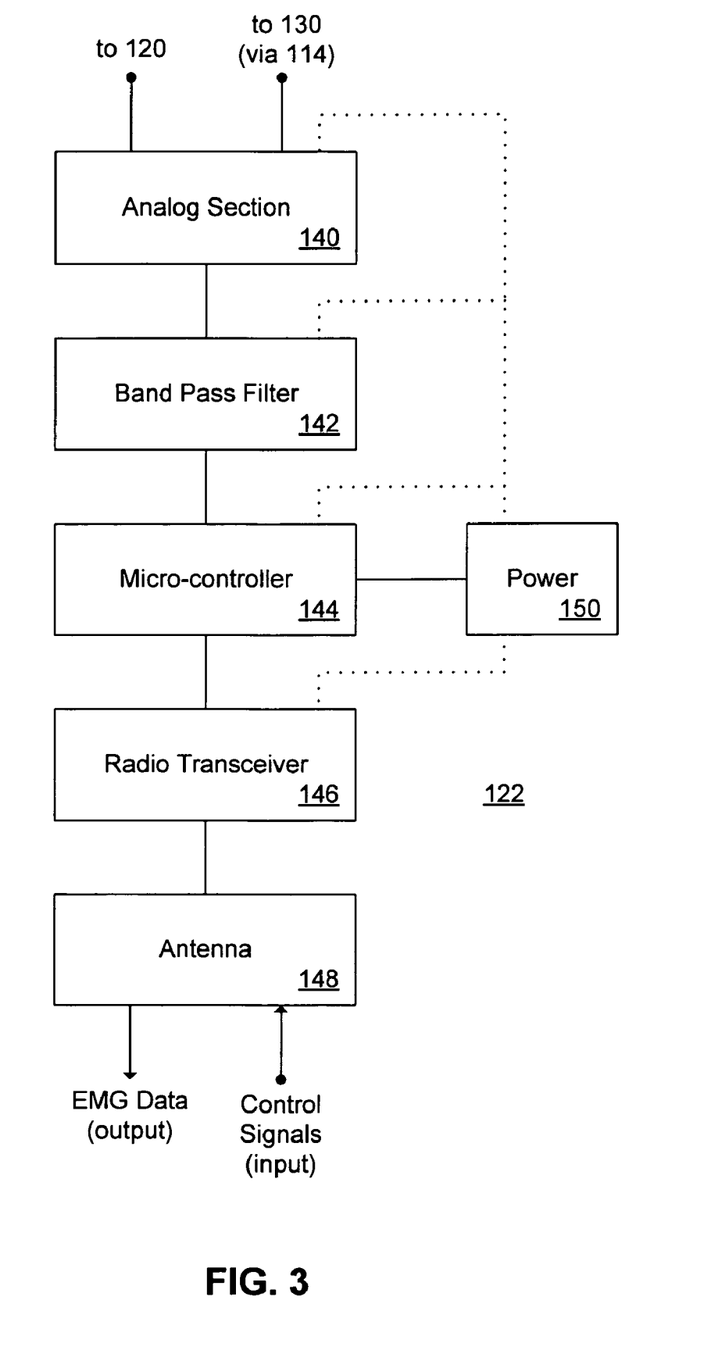
FIG. 3 is a block diagram showing details of the primary sensor unit 110 of FIG. 1.

FIG. 3 is a block diagram of the control unit 122 and related components in the primary sensor unit 110, including an analog section 140, a band pass filter 142, a micro-controller 144, a radio transceiver 146, an antenna 148, and a power supply 150. The control unit 122 and related components of FIG. 3 perform the functions of signal acquisition, signal processing, data generation, data storage, data transmission, data reception, and overall device control.

The analog section 140 performs the initial signal acquisition and processing from the electrodes attached to the primary sensor unit 110 and the secondary sensor unit 112. Among the functions the analog section 140 performs are input conditioning, level shifting, amplification, and differential sensing. The output of the analog section 140 is provided to the band pass filter 142.

The band pass filter 142 allows signals in the range of EMG signals to pass and keeps signals outside the range of EMG signals from passing. According to one embodiment, the band pass filter passes signals in the approximate range between 10 Hz and 200 Hz. According to one embodiment, the band pass filter 142 may be implemented with the TLV2254 operational amplifier from Texas Instruments, Inc. The output of the band pass filter 142 is provided to the micro-controller 144.

The micro-controller 144 performs analog to digital conversion and otherwise controls the primary sensor unit 110. Among the functions the micro-controller 144 performs are conversion of the analog EMG signals from the band pass filter 142 into digital EMG data; storage of the EMG data; data processing of the EMG data into a form for transmission, which may include the addition of identification tags and encryption; transmission control and reception control of the radio transceiver 146; processing and execution of received commands; and power control of the primary sensor unit 110 and its components. According to one embodiment, the micro-controller 144 may be implemented with the ATmega48 micro-controller from Atmel Corp. The processed EMG data is provided to the radio transceiver 146.

The radio transceiver 146 transmits the EMG data collected by the EMG sensor 100 via the antenna 148. In addition, the radio transceiver 146 receives control signals via the antenna 148 and provides the control signals to the micro-controller 144. According to one embodiment, the radio transceiver operates around 850-950 MHz. According to one embodiment, the radio transceiver 146 is coupled to a crystal oscillator, generates a clock signal, and provides the clock signal to the micro-controller 144. According to one embodiment, the radio transceiver 146 may be implemented with the nRF905 Multiband Transceiver from Nordic Semiconductor ASA.

The antenna 148 may be integrated on the printed circuit board to which the micro-controller 144 and other components are attached.

The power supply 150 supplies power to the components of the primary sensor unit 110. According to one embodiment, the power supply 150 is a battery. According to one embodiment, the power supply 150 is a lithium 3.3 V cell having a diameter of approximately 23 mm.

Figure 4:
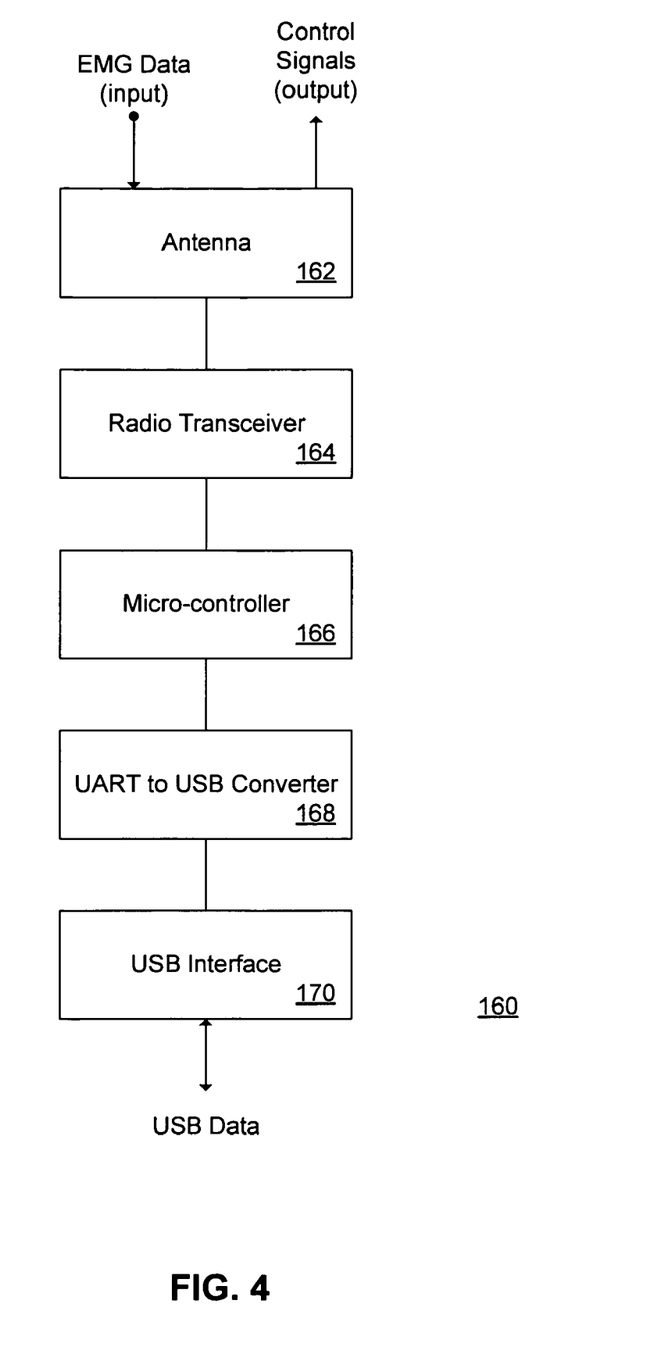
FIG. 4 is a block diagram of a data reception unit according to an embodiment of the present invention.

FIG. 4 is a block diagram of a data reception unit 160. The data reception unit 160 includes an antenna 162, a radio transceiver 164, a micro-controller 166, a UART to USB converter 168, and a USB interface 170. Although the embodiment of FIG. 4 includes universal asynchronous receiver/transmitter (UART) and universal serial bus (USB) data processing capabilities, these functions may be omitted or modified for other data transfer standards according to the particular devices selected or outputs desired.

The antenna 162 and radio transceiver 164 are selected to be compatible with the antenna 148 and radio transceiver 146 of the EMG sensor 100. According to one embodiment, the antenna 162 is an external dipole antenna that is larger than the antenna 148. According to one embodiment, the radio transceiver 164 is coupled to a crystal oscillator, generates a clock signal, and provides the clock signal to the micro-controller 166. The radio transceiver 164 provides the EMG data received from the EMG sensor 100 to the micro-controller 166.

The micro-controller 166 performs data processing on the received EMG data and otherwise controls the data reception unit 160. Among the functions the micro-controller 166 performs are storage of EMG data; data processing of the EMG data received, which may include decryption and processing of identification tags; and reception control and transmission control of the radio transceiver 164. According to one embodiment, the micro-controller 166 may be implemented with the ATmega8 micro-controller from Atmel Corp. The processed EMG data is provided to the UART to USB converter 168.

The UART to USB converter 168 converts the EMG data from the micro-controller 166 into USB format. According to one embodiment, the UART to USB converter 168 may be implemented with the CP2102 UART to USB Bridge from Silicon Laboratories, Inc.

The USB interface 170 is used for physically interfacing the data reception unit 160 to USB ports on other USB devices. According to one embodiment, the data reception unit 160 may be connected to a personal computer (PC) for storage, analysis, and display of the EMG data. In fact, the choice of the USB converter 170 in the data reception unit 160 was so that the data reception unit 160 can easily interface with the USB port on a typical PC.

Figure 5:
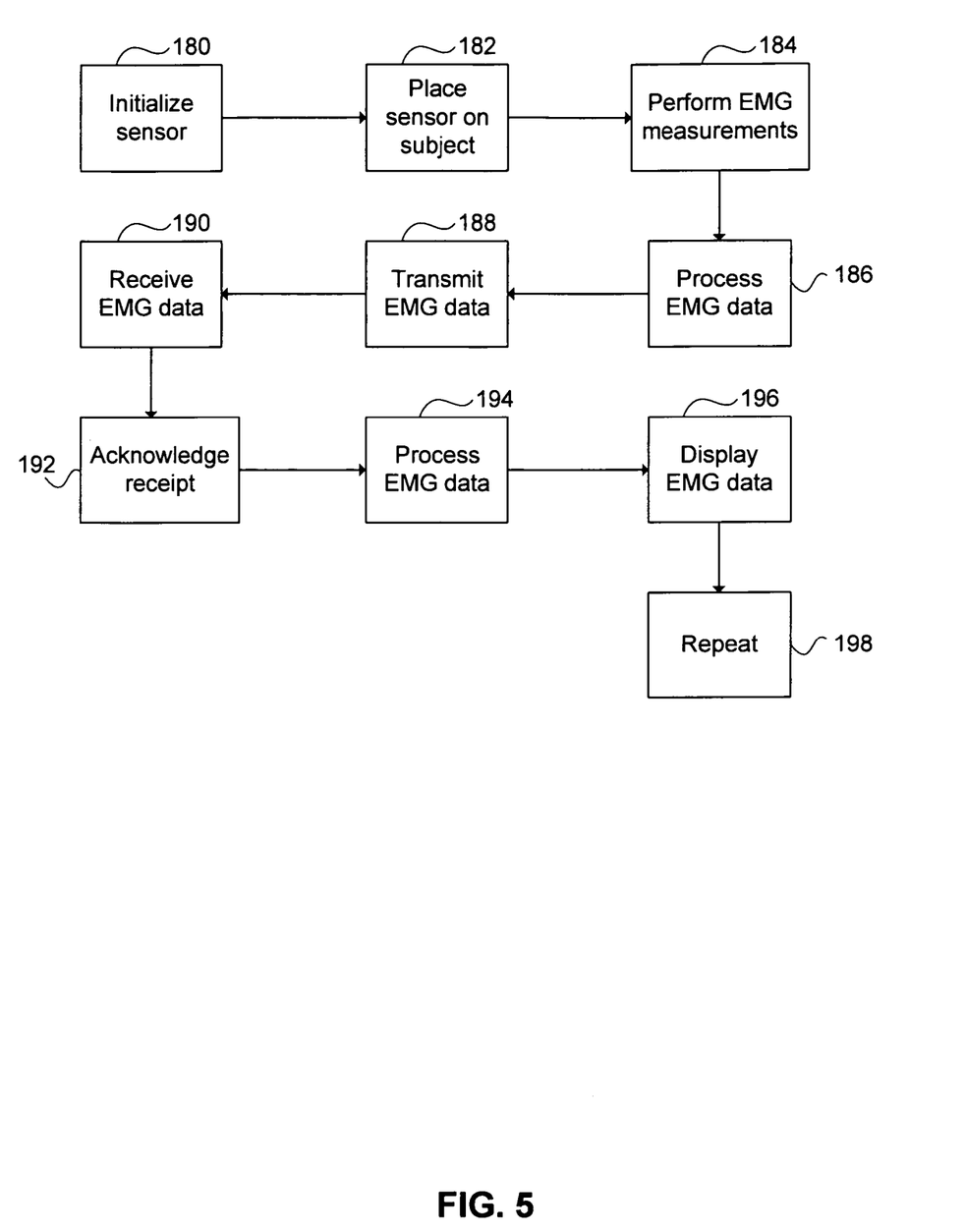
FIG. 5 is a flowchart describing the operation of the EMG sensor 100 and related systems according to an embodiment of the present invention.

FIG. 5 is a flowchart of the basic steps involved in the operation of the EMG sensor 100 and related systems. In step 180, the EMG sensor 100 is initialized. Initialization may occur when a power switch on the EMG sensor 100 is turned on.

In step 182, the EMG sensor 100 is placed on the subject person upon whom the EMG measurements are to be performed. This involves the use of adhesive electrodes as described above with reference to FIG. 1.

In step 184, the EMG sensor 100 performs EMG measurements on the subject. Among the functions performed are differential sensing of the EMG signals, input conditioning, level shifting, and amplification (see FIG. 3 and the description regarding the analog section 140); and band pass filtering of the EMG signals (see FIG. 3 and the description regarding the band pass filter 142).

In step 186, the EMG sensor 100 processes the EMG signals. Among the functions performed are analog to digital conversion of the EMG signals, data processing of the EMG data, and storage of the EMG data prior to transmission (see FIG. 3 and the description regarding the micro-controller 144).

In step 188, the EMG sensor 100 transmits the EMG data to the data reception unit 160. Among the functions performed are loading EMG data into the transmission buffer of the radio transceiver 146; handshaking to prepare the data reception unit 160 for data reception; instructing the radio transceiver 146 to transmit the EMG data in its transmission buffer; transmission of the EMG data to the data reception unit 160; and instructing the radio transceiver 146 to go into receive mode in preparation for receiving a receipt acknowledgement signal (see FIG. 3 and the description regarding the micro-controller 144 and the radio transceiver 146).

In step 190, the data reception unit 160 receives the EMG data from the EMG sensor 100. Among the functions performed are intermediate storage of the EMG data in the reception buffer of the radio transceiver 164 and fetching the EMG data from the reception buffer (see FIG. 4 and the description regarding the radio transceiver 164 and the micro-controller 166).

In step 192, the data reception unit 160 acknowledges receipt of the EMG data to the EMG sensor 100. This involves the micro-controller 166 generating an acknowledgement receipt; the micro-controller 166 instructing the radio transceiver 164 to transmit the acknowledgement receipt; the radio transceiver 146 receiving the acknowledgement receipt; and the micro-controller 144 processing the acknowledgement receipt from the radio transceiver 146 (see FIG. 3, FIG. 4 and the related description regarding these elements). If the EMG sensor 100 fails to receive the acknowledgement receipt, it may attempt to re-transmit the EMG data (see step 188) until the data reception unit 160 acknowledges receipt, or may otherwise indicate a transmission failure.

In step 194, the data reception unit 160 processes the received EMG data. Among the functions performed are data processing of the EMG data, which may include decryption and the processing of identification tags (see FIG. 4 and the description regarding the micro-controller 166).

In step 196, the EMG data is displayed, stored, analyzed, or otherwise acted upon. This involves the micro-controller 166 sending the EMG data to the UART to USB converter 168; the UART to USB converter 170 converting the EMG data into USB format; and the USB interface 170 providing the EMG data to a USB compatible device for display, storage, analysis, or other action (see FIG. 4 and the related description regarding these elements).

In step 198, the process is repeated. For additional measurements on the same muscle, the repetition may start at step 184. For measurements on another muscle (or on another subject), the repetition may start at step 182.

Figure 6A:
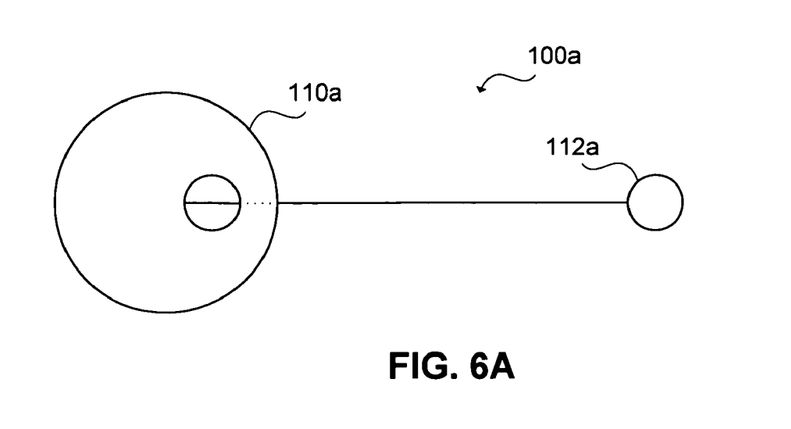
FIGS. 6A-6C are top views of various form factors of the EMG sensor 100 according to various embodiments of the present invention.
Figure 6B:
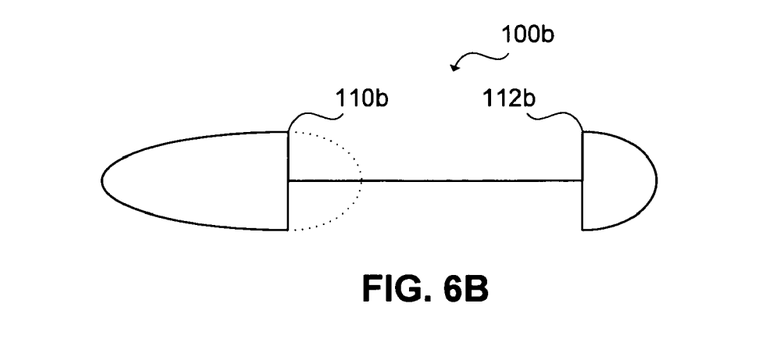
Figure 6C:
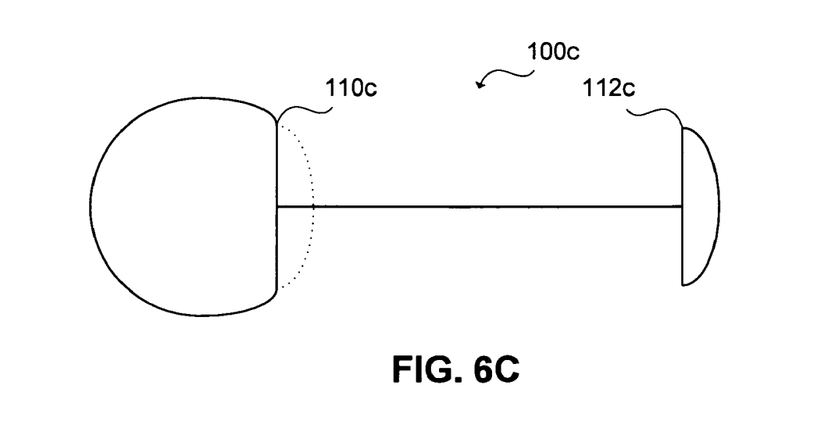

FIGS. 6A-6C show various form factors for the EMG sensor 100. FIG. 6A shows the EMG sensor 100a with the secondary sensor unit 112a removed from an interior portion of the primary sensor unit 110a. FIG. 6B shows the EMG sensor 100b with the secondary sensor unit 112b detached from an outer portion of the primary sensor unit 110b. FIG. 6C shows the EMG sensor 100c with the secondary sensor unit 112c detached from an outer portion of the primary sensor unit 110c.

Figure 7:
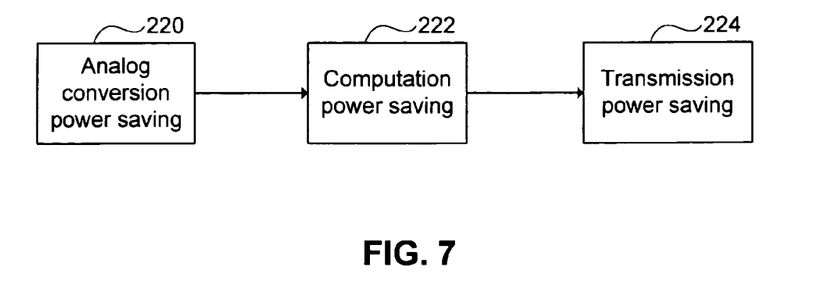
FIG. 7 is a flowchart describing the steps the EMG sensor 100 performs to conserve power according to an embodiment of the present invention.

FIG. 7 is a flowchart describing the steps the EMG sensor 100 performs to conserve power. Referring back to FIG. 3, the control unit 122 includes a micro-controller 144 that controls the supply of power from the power supply 150 to the components of the primary sensor unit 110. In general, the micro-controller 144 performs power shutdowns of device blocks when those device blocks are not in use. Most of the time, the micro-controller 144 instructs all components of the primary sensor unit 110 to power down. Then when it is time for the various components to perform their functions, the micro-controller 144 instructs them to power up. According to one embodiment, the micro-controller 144 may be implemented with the ATmega48 micro-controller from Atmel Corp. The ATmega48 includes a watchdog timer that allows the ATmega48 to power itself down for a time period monitored by the watchdog timer. Thus, in such embodiment, the micro-controller 144 may power itself down.

In step 220, the micro-controller 144 controls the control unit 122 to perform analog conversions. The micro-controller 144 powers up the analog section 140 and the band pass filter 142 (see FIG. 3) to perform analog conversions. The micro-controller 144 powers down the portions of itself that are not involved in analog conversion. The micro-controller 144 instructs the radio transceiver 146 to power down. According to one embodiment, the micro-controller 144 may be implemented with the ATmega48 micro-controller from Atmel Corp. The ATmega48 includes a central programming unit (CPU) and an analog to digital (A/D) converter block. The watchdog timer signals the CPU to power up, the CPU instructs the A/D converter block to power up, the CPU powers down, the A/D converter block performs analog conversions, then the A/D converter block signals the CPU that the analog conversions are complete.

In step 222, the micro-controller 144 controls the control unit 122 to perform computations and to load the transmission buffer in the radio transceiver 146. The micro-controller 144 powers up the portions of itself that are involved in performing computations and loading the transmission buffer. The micro-controller 144 powers down the analog section 140 and the band pass filter 142. According to one embodiment, the micro-controller 144 may be implemented with the ATmega48 micro-controller from Atmel Corp. The CPU in the ATmega48 powers up, instructs the A/D converter block in the ATmega48 to power down, and instructs the radio transceiver 146 to receive data in its transmission buffer.

In step 224, the micro-controller 144 controls the primary sensor unit 122 to perform data transmission. The micro-controller 144 powers up the radio transceiver 146 to transmit the data in the transmission buffer. The radio transceiver 146 transmits the data. The micro-controller 144 instructs the radio transceiver 146 to enter receive mode in anticipation of receiving the receipt acknowledgement signal. Once the receipt acknowledgement signal has been received, the micro-controller 144 powers down itself and the radio transceiver 146. According to one embodiment, the radio transceiver 146 may be implemented with the nRF905 Multiband Transceiver from Nordic Semiconductor ASA.

Figure 8:
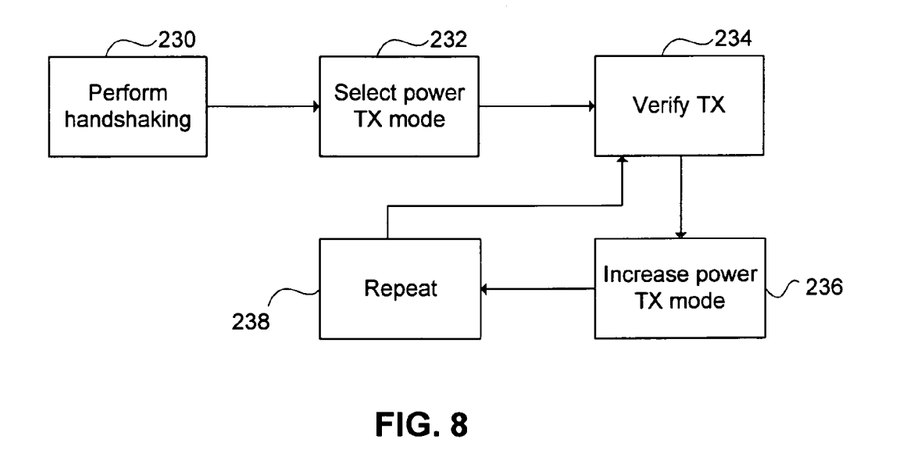
FIG. 8 is a flowchart describing the additional steps the EMG sensor 100 performs to conserve power according to an embodiment of the present invention.

FIG. 8 is a flowchart describing additional steps the EMG sensor 100 performs to conserve power. In general, the micro-controller 144 (see FIG. 3) selects the lowest power transmission mode for the radio transceiver 146 that assures data integrity.

In step 230, the micro-controller 144 instructs the radio transceiver 146 to perform handshaking with the data reception unit 160 (see FIG. 4). The handshaking verifies the integrity of the data link.

In step 232, the micro-controller 144 selects the lowest power transmission mode of the radio transceiver 146 that assures data integrity. According to one embodiment, the radio transceiver 146 may be implemented with the nRF905 Multiband Transceiver from Nordic Semiconductor ASA. In such case, the lowest power transmission mode transmits at approximately −10 dBm, which consumes approximately 9 mA of current.

In step 234, the micro-controller 144 verifies that the data transmitted (that is, which was transmitted at the power transmission mode set in step 232) was received. This verification can involve the receipt of an acknowledgement signal from the data reception unit 160. If the micro-controller 144 verifies receipt of the transmission, the procedure of FIG. 8 ends.

In step 236, if the micro-controller 144 determines that the data transmitted was not received (that is, that step 234 resulted in no verification), the micro-controller 144 instructs the radio transceiver 146 to increase its power transmission mode and to re-transmit the data. An embodiment using the nRF905 has four power transmission modes; the highest mode transmits at +10 dBm, which consumes approximately 30 mA of current.

In step 238, after re-transmission in step 236, the micro-controller 144 repeats step 234. This repetition may continue a programmable number of times. If the programmable number of times is reached without verification of the transmission, the micro-controller 144 instructs the EMG sensor 100 to give up attempting that transmission.

If the EMG sensor 100 has been unsuccessful with a data transmission, it may store the unacknowledged data in the memory of the micro-controller 144. At a later time, after a successful transmission has been completed, the micro-controller 144 may attempt to re-send the data stored in the memory.

Figure 9:
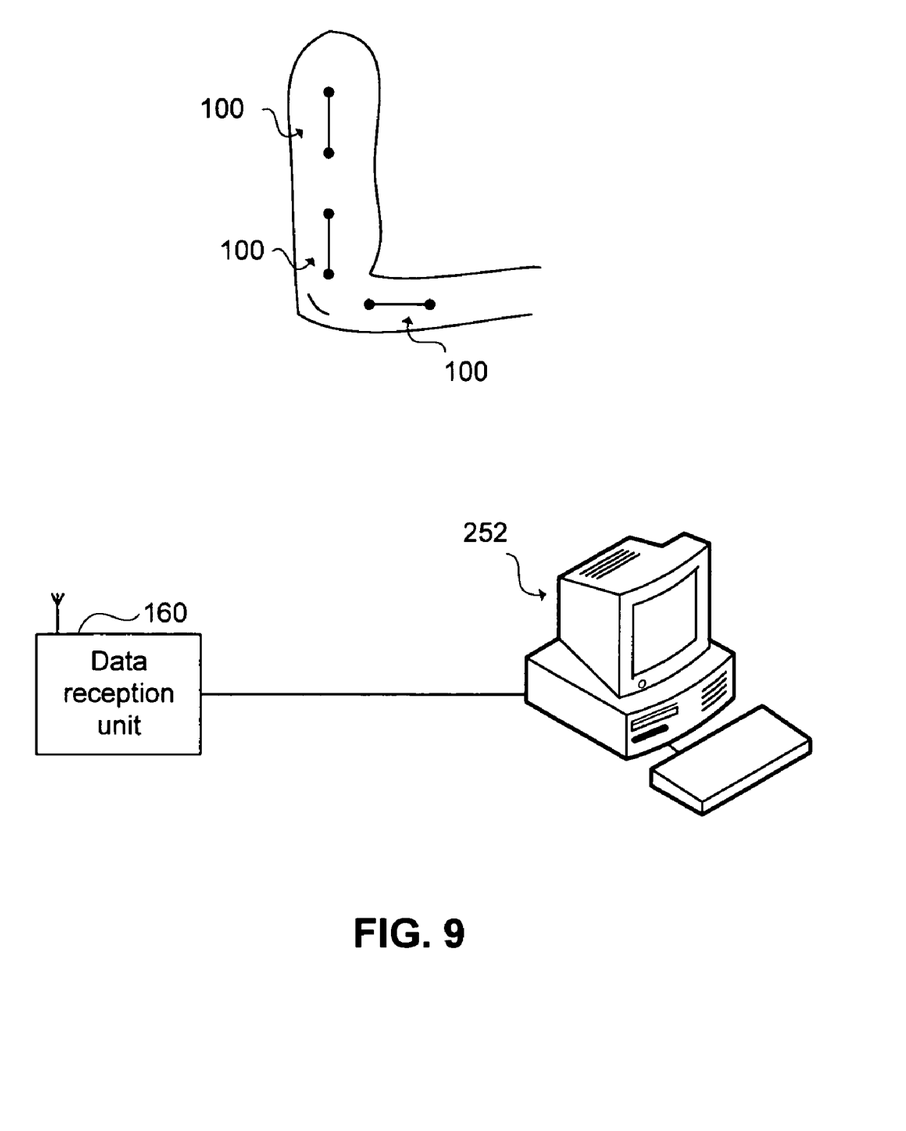
FIG. 9 is a diagram of an EMG analysis system according to an embodiment of the present invention.

FIG. 9 shows an EMG analysis system 250. The EMG analysis system 250 includes one or more EMG sensors 100 (see FIG. 1), the data reception unit 160 (see FIG. 4), and a personal computer 252. The EMG sensors 100 may be placed at numerous locations on a person's body. The data reception unit 160 may be located near or far from the EMG sensors 100, according to the range and desired power consumption level of the EMG sensors 100.

Instead of a personal computer 252, other types of devices may be used for data display (or other functions) according to other embodiments of the present invention. According to one embodiment, a small device such as a personal data assistant (PDA) may communicate wirelessly with the data reception unit 160. The PDA may include a screen for displaying the EMG data. The PDA may also include a visual indicator, auditory indicator, or vibratory indicator that warns the user when the EMG data falls outside of an accepted range of parameters. For example, the PDA may buzz when the EMG data indicates that the user is performing an activity that may result in RSI.

Figure 10:
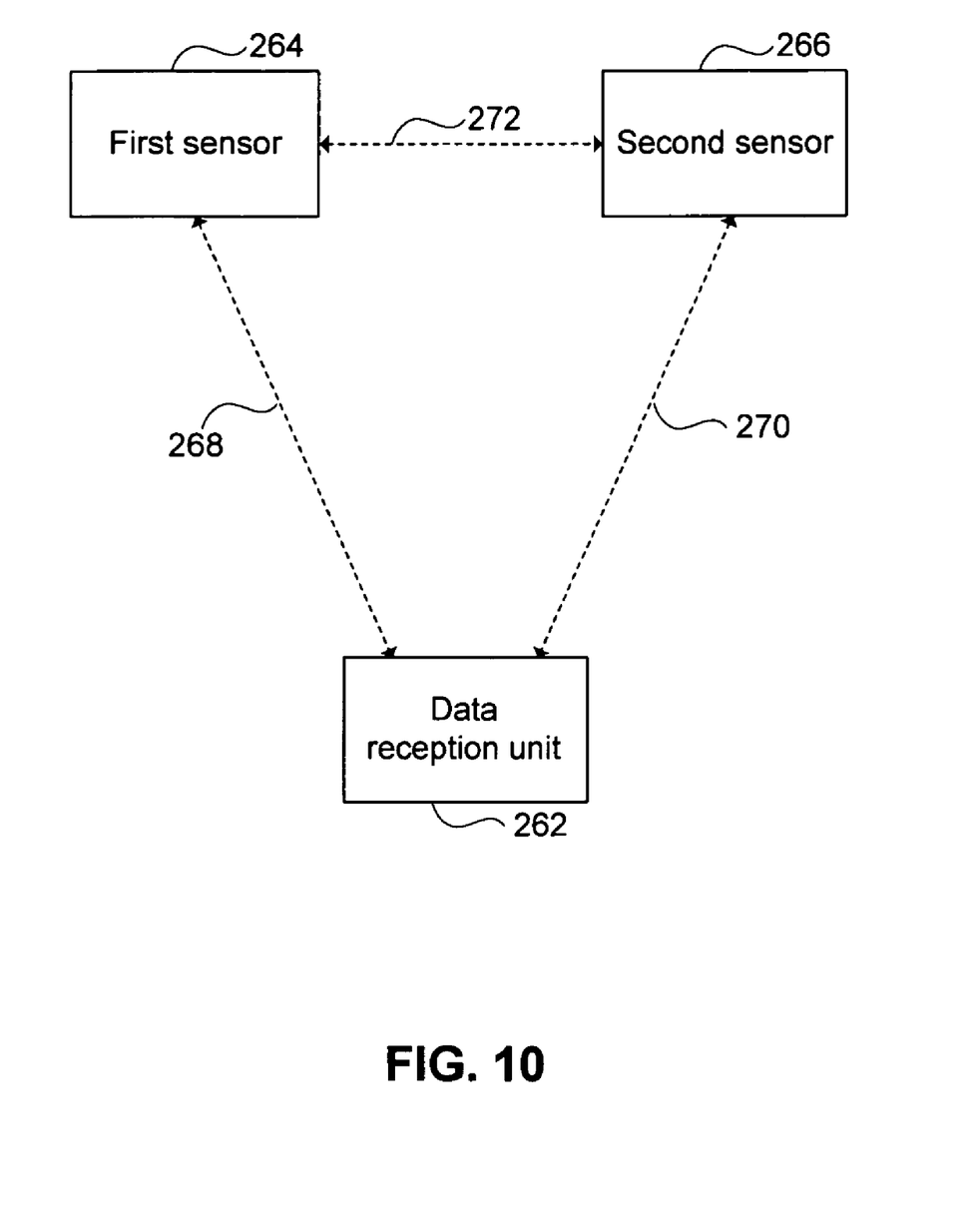
FIG. 10 is a block diagram of a wireless EMG sensor system according to another embodiment of the present invention.

FIG. 10 is a block diagram of a wireless EMG sensor system 260 according to another embodiment of the present invention. The wireless EMG system 260 includes a data reception unit 262, a first wireless EMG sensor 264, and a second wireless EMG sensor 266. The data reception unit 262 is similar to the data reception unit 160 (see FIG. 4 and FIG. 9). The first wireless EMG sensor 264 is similar to the primary sensor unit 110 (see FIG. 1) and contains components similar to the control unit 122 (see FIG. 3). The second wireless EMG sensor 266 is also similar to the primary sensor unit 110 (see FIG. 1) and contains components similar to the control unit 122 (see FIG. 3). The system 260 may operate in one or both of the operational modes discussed below.

In a first mode of operation, the first wireless EMG sensor 264 and the second wireless EMG sensor 266 both communicate directly with the data reception unit 262. The first wireless EMG sensor 264 communicates with the data reception unit 262 over a wireless link 268, and the second wireless EMG sensor 266 communicates with the data reception unit 262 over a wireless link 270. A flexible connector (such as the flexible connector 114 of FIG. 1) is not required.

In a second mode of operation, the first wireless EMG sensor 264 operates as a master unit and the second wireless EMG sensor 266 operates as a slave unit. The first wireless EMG sensor 264 communicates with the data reception unit over the wireless link 268. The second wireless EMG sensor 266 communicates with the first wireless EMG sensor 264 over a wireless link 272. The first wireless EMG sensor 264 acts as an intermediary between the second wireless EMG sensor 266 and the data reception unit 262. A flexible connector (such as the flexible connector 114 of FIG. 1) is not required. As a variation on this embodiment, the first wireless EMG sensor 264 and the second wireless EMG sensor 266 may include infrared transceiver units, and may communicate via infrared signals over the wireless link 272. In such an embodiment, an infrared transceiver unit may replace the radio transceiver and antenna (see FIG. 3) of the second wireless EMG sensor 266, and an infrared transceiver unit may be added to the control unit (see FIG. 3) of the first wireless EMG sensor 264.

As discussed above, the embodiments of the present invention overcome many limitations of existing wireless EMG sensors. Embodiments of the present invention are adjustable, unlike many existing wireless EMG sensors. Embodiments of the present invention are reusable, unlike many existing wireless EMG sensors. Embodiments of the present invention do not require a ground electrode, unlike many existing wireless EMG sensors. Embodiments of the present invention conserve power and extend battery life as compared to other existing wireless EMG sensors.

The above description illustrates various embodiments of the present invention along with examples of how aspects of the present invention may be implemented. The above examples and embodiments should not be deemed to be the only embodiments, and are presented to illustrate the flexibility and advantages of the present invention as defined by the following claims. Based on the above disclosure and the following claims, other arrangements, embodiments, implementations and equivalents will be evident to those skilled in the art and may be employed without departing from the spirit and scope of the invention as defined by the claims. The terms and expressions that have been employed here are used to describe the various embodiments and examples. These terms and expressions are not to be construed as excluding equivalents of the features shown and described, or portions thereof, it being recognized that various modifications are possible within the scope of the appended claims.

What is claimed is:

1. A two piece wireless electromyography (EMG) sensor, comprising:
    a first piece of said two piece sensor comprising a first sensor portion that includes a first housing, first measurement attachment point, a wireless transmitter, and a control circuit coupled to said first measurement attachment point and said wireless transmitter, wherein said control circuit controls said wireless EMG sensor;
    a second piece of said two piece sensor comprising a second housing, a second sensor portion that includes a second measurement attachment point; and
    a retractable connector that connects the first sensor portion and the second sensor portion, wherein the retractable connector adjusts for a variety of measurement distances between the first measurement attachment point and the second measurement attachment point corresponding to a variety of different sized muscles to be measured of a subject, wherein the variety of measurement distances vary from a position where the first housing is directly adjacent, or relatively close, to the second housing for EMG measurements of a relatively small muscle of the subject to a position where the first housing is separated by a distance from the second housing for EMG measurements of a relatively large muscle of the subject,
    wherein the retractable connector further includes a spool and a flexible connector that provides electrical communication between the first and second pieces of the two piece sensor, wherein when said EMG sensor is not in use the spool collects the flexible connector therearound within the first or second housing, and wherein when the EMG sensor is in use the spool allows the flexible connector to be drawn out and retracted according to the variety of measurement distances related to different muscle size thereby retaining excess length of the flexible connector within the first or second housing during active movement by the subject such that the excess cable does not impair or affect the active movement of the subject, and
    wherein said control circuit controls collection of EMG measurements between said first measurement attachment point on said first piece of said two piece sensor and said second measurement attachment point on said second piece of said two piece sensor, and controls said wireless transmitter to transmit said EMG measurements having been collected.

2. The wireless EMG sensor of claim 1, wherein said first sensor portion further includes the spool around which said adjustable connector may be manually wound and unwound.

3. The wireless EMG sensor of claim 1, wherein said adjustable connector electrically couples said second measurement attachment point and said control circuit.

4. The wireless EMG sensor of claim 1, wherein said first sensor portion further includes a wireless receiver for receiving control signals, and wherein said control circuit is responsive to said control signals for controlling said wireless EMG sensor.

5. The wireless EMG sensor of claim 1, wherein said wireless transmitter comprises a wireless transceiver, wherein said wireless transceiver receives control signals, and wherein said control circuit is responsive to said control signals for controlling said wireless EMG sensor.

6. The wireless EMG sensor of claim 1, wherein said first sensor portion further includes an antenna coupled to said wireless transmitter.

7. The wireless EMG sensor of claim 1, wherein said first sensor portion further includes an analog section coupled to said first measurement attachment point and to said control circuit, and wherein said analog section performs differential sensing of said EMG measurements.

8. The wireless EMG sensor of claim 7, further comprising:
an adjustable connector that couples said analog section to said second measurement attachment point.

9. The wireless EMG sensor of claim 1, wherein said first sensor portion further includes a band pass filter coupled to said first measurement attachment point and to said control circuit, and wherein said band pass filter filters said EMG measurements.

10. The wireless EMG sensor of claim 1, wherein said control circuit processes said EMG measurements, provides said EMG measurements to said wireless transmitter, and performs reception acknowledgement functions according to whether an acknowledgement receipt of said EMG measurements is received.

11. The wireless EMG sensor of claim 1, wherein said control circuit controls power saving by said wireless EMG sensor by selectively powering down selected components of said first sensor portion.

12. The wireless EMG sensor of claim 1, wherein said control circuit controls power saving by said wireless EMG sensor during analog conversions by powering down selected blocks of said control circuit that are not involved in said analog conversions.

13. The wireless EMG sensor of claim 1, wherein said control circuit controls power saving by said wireless EMG sensor during analog conversions by powering down said wireless transmitter.

14. The wireless EMG sensor of claim 1, wherein said first sensor portion includes an analog section and a band pass filter, wherein said control circuit controls power saving by said wireless EMG sensor during data computations by powering down said analog section and said band pass filter.

15. The wireless EMG sensor of claim 1, wherein said control circuit controls power saving by said wireless EMG sensor during data transmission by operating in a first power consumption mode during data transmission and a second power consumption mode in anticipation of a receipt acknowledgement signal.

16. The wireless EMG sensor of claim 1, wherein said control circuit controls power saving by said wireless EMG sensor during data transmission by directing said wireless transmitter to transmit said EMG measurements at a minimal power level for reception.

17. The wireless EMG sensor of claim 1, wherein said control circuit controls power saving by said wireless EMG sensor during analog conversions by powering down selected blocks of said control circuit that are not involved in said analog conversions.

18. The wireless EMG sensor of claim 1, wherein said control circuit controls power saving by said wireless EMG sensor during analog conversions by powering down said wireless transmitter.

19. The wireless EMG sensor of claim 1, wherein said wireless EMG sensor further includes an analog section and a band pass filter, wherein said control circuit controls power saving by said wireless EMG sensor during data computations by powering down said analog section and said band pass filter.

20. The wireless EMG sensor of claim 1, wherein said control circuit controls power saving by said wireless EMG sensor during data transmission by operating in a first power consumption mode during data transmission and a second power consumption mode in anticipation of a receipt acknowledgement signal.

21. The wireless EMG sensor of claim 1, wherein said control circuit controls power saving by said wireless EMG sensor during data transmission by directing said wireless transmitter to transmit said EMG measurements at a minimal power level for reception.

22. The wireless EMG sensor of claim 1, wherein the spool is disposed in the first housing along with the control circuit.

23. The wireless EMG sensor of claim 1, wherein the antenna is integrated on a printed circuit board along with the control circuit.

24. The wireless EMG sensor of claim 1, wherein the first piece and the second piece are configured such that the second piece is attached to an interior portion of the first piece when not in use and is detachable from the interior portion of the first piece when in use.

25. The wireless EMG sensor of claim 1, wherein the first piece and the second piece are configured such that the second piece is attached to an exterior portion of the first piece when not in use and is detachable from the exterior portion of the first piece when in use.

26. The wireless EMG sensor of claim 1, wherein the spool is maintained at a tension.

27. A system for collecting and displaying electromyography (EMG) information, comprising:
the wireless EMG sensor of claim 1; and
a data display device, coupled to said data reception unit, that displays said EMG measurements.

28. The system of claim 27, wherein said wireless transmitter comprises a first wireless transceiver, wherein said wireless receiver comprises a second wireless transceiver, wherein said reception control circuit controls said data reception unit to transmit an acknowledgement receipt after said data reception unit has received said EMG measurements, and wherein said control circuit performs reception acknowledgement functions according to whether said acknowledgement receipt is received.

* * * * *